(12) United States Patent
Solomon

(10) Patent No.: US 7,628,057 B1
(45) Date of Patent: Dec. 8, 2009

(54) APPARATUS AND METHOD FOR DETERMINING VAPOR PRESSURE OF MULTI-COMPONENT LIQUIDS

(76) Inventor: Ahmad G. Solomon, P.O. Box 821341, Houston, TX (US) 77282

( * ) Notice: Subject to any disclaimer, the term of this patent is extended or adjusted under 35 U.S.C. 154(b) by 24 days.

(21) Appl. No.: 11/893,561

(22) Filed: Aug. 16, 2007

Related U.S. Application Data

(60) Provisional application No. 60/873,524, filed on Dec. 7, 2006.

(51) Int. Cl.
*G01N 7/14* (2006.01)

(52) U.S. Cl. ..................................................... 73/64.45

(58) Field of Classification Search ............... 73/64.45, 73/64.46, 64.78, 61.78
See application file for complete search history.

(56) References Cited

U.S. PATENT DOCUMENTS

| | | | | |
|---|---|---|---|---|
| 3,499,317 | A | * | 3/1970 | Hook .......................... 73/64.45 |
| 4,332,159 | A | * | 6/1982 | Chin et al. .................. 73/64.45 |
| 4,543,819 | A | * | 10/1985 | Chin et al. ..................... 137/88 |
| 4,733,557 | A | * | 3/1988 | Baillie et al. ............... 73/64.46 |
| 4,783,989 | A | * | 11/1988 | Reed .......................... 73/64.45 |
| 4,901,559 | A | * | 2/1990 | Grabner ..................... 73/64.45 |
| 5,172,586 | A | | 12/1992 | Reed .......................... 73/64.45 |
| 5,329,811 | A | * | 7/1994 | Schultz et al. ............ 73/152.02 |
| 5,499,531 | A | | 3/1996 | Henderson ................. 73/64.45 |
| 5,563,339 | A | * | 10/1996 | Compton et al. ........... 73/64.45 |
| 5,635,631 | A | * | 6/1997 | Yesudas et al. ............ 73/61.46 |
| 5,637,791 | A | | 6/1997 | Alonso ...................... 73/61.78 |
| 5,663,492 | A | * | 9/1997 | Alapati et al. .............. 73/64.45 |
| 5,889,202 | A | | 3/1999 | Alapati et al. .............. 73/64.45 |
| 6,223,588 | B1 | * | 5/2001 | Burgass et al. ............. 73/53.01 |

OTHER PUBLICATIONS

American Society for Testing and Materials, Standard Test Method for Vapor Pressure of Petroleum Products (Reid Method), Jun. 1999, p. 1-10.
American Society for Testing and Materials, Standard Test Method for Vapor Pressure of Petroleum Products (Mini Method),Mar. 1999, p. 1-5.
American Society for Testing and Materials, Standard Test Method for Crude Oil: VPCR (Expansion Method), Mar. 1999, p. 1-5.

* cited by examiner

*Primary Examiner*—John Fitzgerald
(74) *Attorney, Agent, or Firm*—Elizabeth R. Hall

(57) ABSTRACT

A system that allows an operator to determine the true vapor pressure of a liquid composition from the bubble-point pressure for a given temperature at which the lightest component starts to flash includes a heated chamber with a retractable plunger. A sample of the liquid to be tested is trapped in a chamber at a pressure above the bubble-point pressure. A plunger inserted into the chamber gradually reduces the chamber internal pressure by retracting the plunger out of the chamber at a uniform (synchronous) speed from the start to the resting plunger rod position. The chamber pressure is recorded at each pressure increment reduction. The bubble point-pressure is determined from the point of inflection in the pressure decline curve.

20 Claims, 5 Drawing Sheets

APPARATUS AND METHOD FOR DETERMINING VAPOR PRESSURE OF MULTI-COMPONENT LIQUIDS

CROSS REFERENCE TO RELATED APPLICATIONS

This application claims priority to pending U.S. Patent Application Ser. No. 60/873,524, filed Dec. 7, 2006 by inventor Ahmad G. Solomon and entitled "System and Method for Determining Vapor Pressure of Multi-Component Liquids."

BACKGROUND OF THE INVENTION

1. Field of the Invention

The present invention relates to vapor pressure and more specifically to an apparatus and method of measuring the vapor pressure of multi-component liquids.

2. Description of the Related Art

Prior to the 1940s, light hydrocarbons and hazardous gases byproducts were considered undesirable in various petrochemical products. These undesirable byproducts were removed by venting them into the atmosphere during the processing of various hydrocarbons. As the public became increasingly concerned about the environmental and safety issues related to the venting of these gases, government agencies began to regulate the environmental emission of such gaseous byproducts of chemical processes.

In order to control the emission of these gaseous byproducts, the petrochemical industry needed to be able to determine the circumstances governing the release of such gaseous byproducts from multi-component petrochemical liquids. Since the vapor pressure of liquids is proportional to the pressure at which liquids will start to flash out of the liquid phase into a gaseous phase, the petrochemical industry was forced to look for simple and practical procedures to determine the pressure at which the first gas bubble was released from a multi-component fluid (referred to as the "bubble point" in the oil industry and the "boiling point" in the chemical industry).

From the 1930s to the late 1960s, vapor losses were primarily predicted by the Reid vapor pressure (RVP) method in accordance to ASTM-323 standards. In the 1950s and 1960s, it became obvious that there were errors in predicting vapor pressures in accordance with the ASTM-323 standards. As a result, the American Petroleum Institute (API) developed Monograph 2517 setting out corrections for minimizing errors in predicting vapor pressures. However, over the years it became apparent that even these corrections fell short of the industry and environmental requirements. Thus, the API Monograph 2517 has become obsolete over the past few years. Then in the 1980s, various products and testing procedures were developed to predict the vapor pressures of multi-component liquids at specified temperatures. Several of these processes and products are described in U.S. Pat. Nos. 5,637,791 (Alonso), 5,499,531 (Henderson), 5,889,202 (Alapati), 4,905,505 (Reed-1) and 5,172,586 (Reed-2).

Alonso utilizes an online analyzer to continuously determine the vapor pressure of a multi-component liquid. The online analyzer measures the highest pressure of the liquid at a given temperature at which the lightest component of the liquid starts to flash. Alonso's analyzer utilizes an upstream aeration or density measurement means and a pressure reducing means (such as capillary tubing) to reduce the pressure to the vapor pressure of the liquid without creating pressure recovery. However, this method has proved unsuitable for it is unable to control the pressure of the liquid as necessary for really accurate determinations of vapor pressure.

The Henderson patent discloses a system and method for calculating the composition of a liquid hydrocarbon using an iterative mathematical algorithm. The Henderson system is a time consuming process and requires expensive equipment, such as a chromatograph and a computer, to calculate the fluid composition and the liquid vapor pressure. Yet, the Henderson system does not provide for the direct measurement of the vapor pressure of a fluid.

Alapati describes a continuous direct analysis of an influent stream of liquid hydrocarbons through a liquid/gas separation chamber, a constant flow liquid influent means, influent and effluent flow metering means, and means for sensing the composition of the gaseous effluent. However, the accuracy of the Alapati equipment has not been verified.

Reed (Reed-1 and 2) determines true vapor pressure of a liquid composition by using a piston and cylinder apparatus to trap a liquid sample, then expanding the chamber volume in multiple steps and recording the multiple pressure drops. A resultant pressure is determined using the least square method of approximation. Then the result and pressure values are extrapolated to determine the true vapor pressure using a straight-line approximation. The apparatus does hot measure the vapor pressure directly and, therefore, is not as accurate as desired.

Even today, many engineers and industry personnel are still confused whether RVP by ASTM-323 procedures is reported in absolute or gauge pressure readings. Today almost all of the results are reported as True Vapor Pressures (TVP) and not RVP, thereby eliminating the conversion from RVP to TVP and much of the prior confusion.

There is a continuing need for a simple and rapid method and apparatus for accurately determining the bubble-point pressure at a constant temperature of a multi-component liquid.

SUMMARY OF THE INVENTION

A system and method for determining the true vapor pressure of a liquid composition from the bubble point pressure for a given temperature at which the lightest component starts to flash. A sample of the liquid to be tested is trapped (or captured) in a chamber at a pressure above the bubble-point pressure. A plunger is provided to increase the fluid volume in the chamber which gradually reduces the chamber internal pressure by retracting (stroking) the plunger out of the chamber at a uniform (synchronous) speed from the start to the resting plunger position. The chamber pressure is recorded at each pressure increment reduction. The bubble point-pressure is determined from the point of inflection in the curve plotting pressure decline against elapsed time or plunger position.

BRIEF DESCRIPTION OF THE DRAWINGS

For a more complete understanding of the present invention, and the advantages thereof, reference is now made to the following descriptions taken in conjunction with the accompanying drawings, in which.

Figure 1:
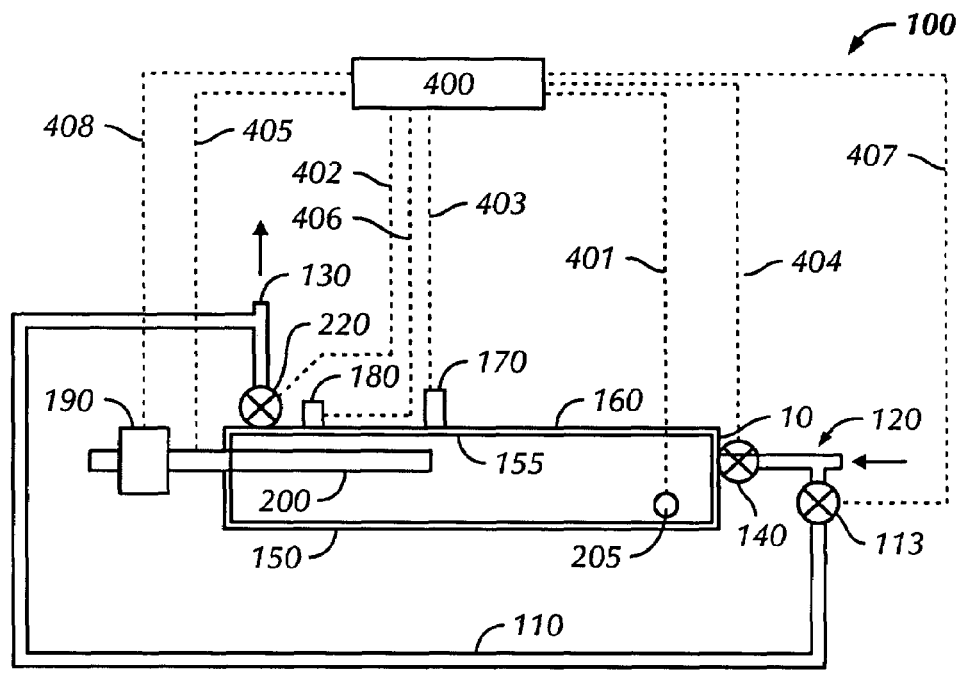
FIG. 1 is a schematic representation of a side view of one embodiment of the vapor pressure determination system.

It is noted that like reference characters designate like or similar parts throughout the drawings. The figures, or drawings, are not intended to be to scale. For example, purely for the sake of greater clarity in the drawings, wall thicknesses and spacings are not dimensioned as they actually exist in the assembled embodiments.

DESCRIPTION OF THE PREFERRED EMBODIMENTS APPARATUS

The present invention relates to an apparatus and method for determining the true vapor pressure (TVP) of a liquid composition from the bubble point pressure for a given temperature at which the lightest component starts to flash. A sample of the liquid to be tested is contained within a chamber at a pressure above the bubble-point pressure. A retractable plunger is provided to increase the liquid volume within the chamber by retracting the plunger out of the chamber at a uniform rate and at a low speed, thereby gradually increasing the liquid volume and decreasing the internal pressure of the chamber. The chamber pressure is continuously recorded as a function of plunger position or time during the pressure reduction. The bubble point-pressure is determined from the point of inflection in the curve plotting pressure decline against elapsed time or plunger position.

Vapor Pressure Determination System

Figure 2:
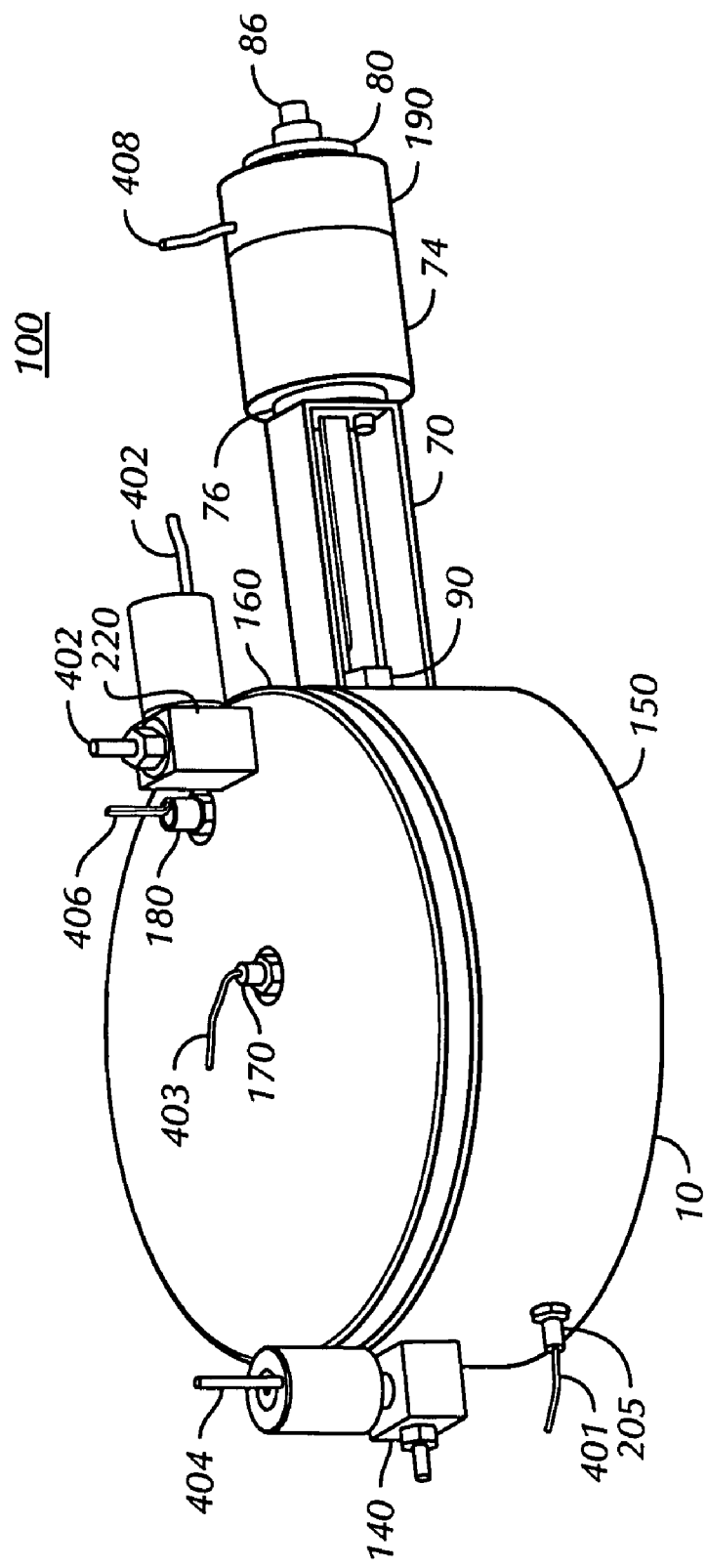
FIG. 2 is a isomeric projection of one embodiment of the vapor pressure determination system.

The major components of a preferred embodiment of the true vapor pressure (TVP) determination system 100 are schematically illustrated in FIG. 1 and are shown in more detail in FIG. 2. The major components of the TVP determination system 100 include a chamber 150, a chamber lid 160, a liquid intake line 120 controlled by a liquid intake valve 140, a liquid purge line 130 controlled by a liquid purge valve 220, a bypass line 110 controlled by a bypass valve 113, a temperature stabilizer 205 such as a heating element 210 for the chamber, a pressure sensor 170, a temperature sensor 180, a retractable plunger 200, and a drive motor 190 for reciprocating the plunger.

The chamber lid 160 fits on the chamber 150 to form a sealed chamber assembly 10 to provide an enclosed volume which serves as the sample space for the vapor pressure determination of a liquid sample. The chamber lid 160 is tightly secured to the top rim of the chamber 150 and sealed with a gasket 30. Control of the system is provided by a control means 400 which may be a programmable linear controller (PLC), a computer, or a manual switching device.

The body of chamber 150 is typically cylindrical with a vertical axis and a diameter approximately three or more times its axial length. Although a cylindrical configuration is not required, the cylindrical configuration provides a large surface area at the point of contact between the liquid surface and the chamber lid 160. Regardless of the shape of the chamber 150, a large contact surface area is preferred. The larger the contact surface area is the more accurate the vapor pressure measurement. A preferred embodiment of the chamber has a width to height ratio of about 3.0 or more, where the large surface area and relatively low height of the chamber assembly 10 provides a short travel distance for gas bubbles to reach the point of contact between the liquid surface and the chamber lid 160.

The vapor pressure determination system 100 includes a flow circuit for the liquid composition to be tested. The liquid composition flows into the chamber 150 through a liquid intake line 120. The introduction of the liquid composition into the chamber assembly 10 is controlled by a liquid intake valve 140 sealingly mounted on one side of the chamber 150. The liquid intake line 120 is externally attached to the liquid intake valve 140. The liquid composition flows out of the chamber assembly 10 through a liquid purge line 130 controlled by a liquid purge valve 220 sealingly mounted on the chamber lid 160. The liquid purge valve 220 and the liquid purge line 130 are preferably mounted on the chamber lid 160 distal to the liquid intake valve 140.

A bypass flow line 110, external to the chamber assembly 10, runs from the liquid intake flow line 120 to the liquid purge line 130. A bypass valve 113 controls the flow of the liquid composition through the bypass flow line 110. When the liquid intake valve 140 and the purge valve 220 are closed and the bypass valve 113 is open the liquid composition flows through the bypass line 110 and circumvents the chamber assembly 10.

The chamber 150 uses the liquid intake line 120 and the liquid purge line 130 to receive, isolate and discharge/purge the multi-component liquid sample to be tested for vapor pressure determination. The system 100 is designed to handle volatile multi-component liquids having different vapor pressures. The system 100 is particularly suitable to sampling and testing crude oil and petroleum products.

Typically, the liquid intake valve 140, the purge valve 220, and the bypass valve 113 are standard commercially available actuated two-position, two-way ball valves having electric actuators and electrical control lines supplying the actuators. All of the valves are preferably directly mounted on the chamber 150 or the chamber lid 160 to avoid trapping vapor in fluid lines. The ball valves 140, 220, and 113 function as on/off controls for fluid flow through interconnected tubing by appropriately activating their actuators to align or move out of alignment the ball flow passages relative to the valve body flow passages The temperature stabilizer 205 is used to maintain the temperature of the liquid being tested at a constant value. The temperature stabilizer will include heating and cooling elements as the liquid to be tested may require heating or cooling. Most of the time the liquid entering the chamber assembly 10 for testing will need to be heated; however, if the temperature of the liquid is above the desired temperature before entering the chamber assembly then the liquid will be chilled by the cooling element in the temperature stabilizer 205. In some embodiments, the liquid will be prechilled to below the desire temperature before entering the chamber assembly 10, so that the heating element in the chamber can maintain a constant temperature of the liquid within the chamber assembly 10. Power and communication to the temperature stabilizer 205 is selectably provided through the temperature communication cable 401.

A heating element 210 is often employed by the system 100 to uniformly heat the liquid sample in the chamber assembly 10 to a desired temperature. Temperature is monitored throughout the test cycle by the temperature sensor 180 and the liquid composition is maintained at a constant temperature using the heating element 210 which is equipped with a thermostat (not shown) to facilitate setting the system temperature at the desired level as required by the testing procedures.

Figure 3:
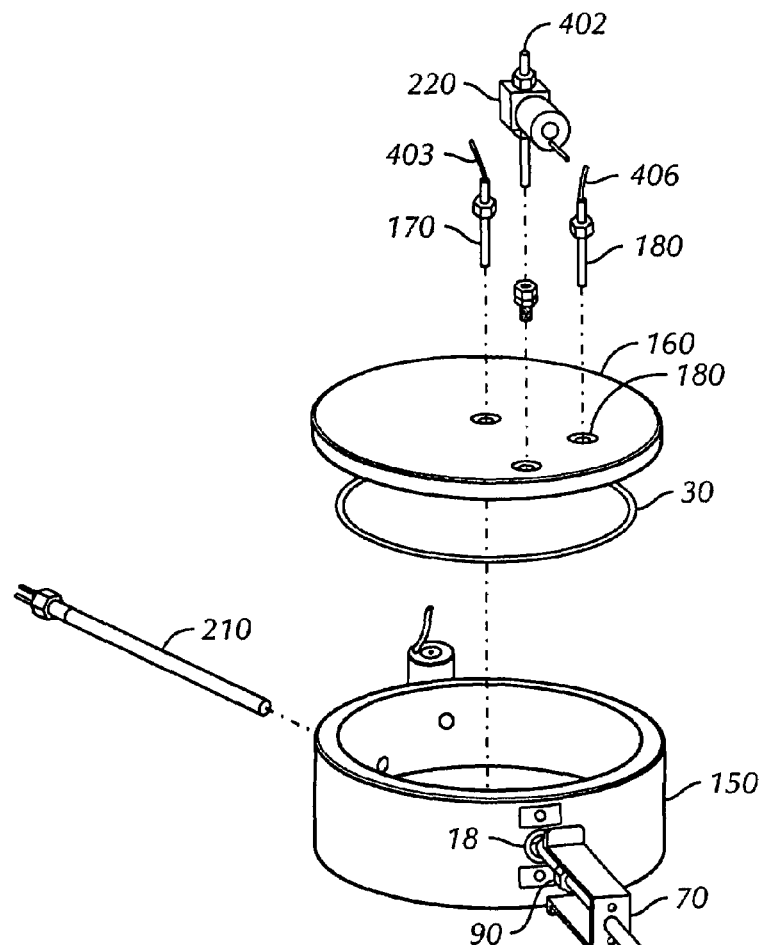
FIG. 3 is an oblique exploded view of one embodiment of the vapor pressure determination system illustrating the major components of the system.
Figure 4:
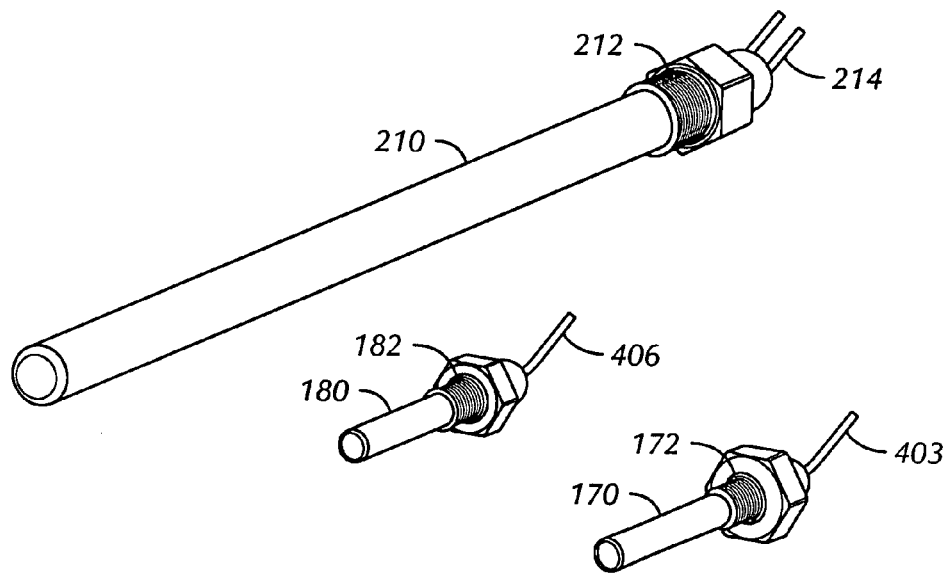
FIG. 4 is an oblique view of one embodiment of the cartridge heater, the pressure sensor, and the temperature gauge.

One embodiment of the heating element 210 uses a standard commercially available cartridge heater, as illustrated in FIGS. 3 and 4, which penetrates either the chamber 150 or the chamber lid 160 close to the liquid intake valve. Typically, the cartridge heater is sealingly connected to the chamber 150 by means of its external threads and associated O-ring 212 engaged with a heater port in the chamber 150. The cartridge heater 210 extends into the interior of the chamber assembly 10 such that it is not in alignment with the plunger 200, so that the plunger can extend throughout the chamber assembly 10 without obstruction. The cartridge heater 210 is generally an internally sealed elongated cylindrical assembly having internal heater wires and insulation inside of a thin walled tubular body. Power and communication to the cartridge heater 210 is selectably provided through the temperature communication cable 401.

Another embodiment of the temperature stabilizer 205 uses a commercially available external metal jacket (not shown). One advantage to using the metal jacket heater and/or cooler is that it can be removed when the chamber assembly 10 is taken off line for cleaning or maintenance. Another advantage of the external metal jacket is that by encompassing the external surface of the chamber assembly 10, the jacket will ensure that the entire chamber assembly remains at a constant temperature.

A standard commercially available temperature sensor 180 is sealingly engaged in the chamber assembly 10 by means of its threads and O-ring 182. The temperature sensor can penetrate either the chamber 150 or the chamber lid 160. Preferably the temperature sensor 180 is positioned in the chamber lid 160 close to the liquid purge valve to ensure temperature regulation near the top of the chamber assembly 10.

The temperature sensor 180 is best seen in FIG. 4. The body of temperature sensor 180 is a sealed elongated cylindrical tube with closed ends and having a sensing element (not shown) inside. The sensing element typically would be a thermocouple, but thermistors or other types of sensors could be used. Power and communication to the temperature sensor 180 are provided by means of temperature sensor communication cable 406.

The pressure sensor 170 monitors the pressure in the chamber assembly 10 throughout the test cycle. One embodiment of the pressure sensor is a standard commercially available pressure sensor 170 sealingly engaged in a pressure sensor port in the chamber lid 160 by means of its threads and O-ring 172. The pressure sensor 170 is best seen in FIG. 4. The body of pressure sensor 170 is a sealed elongated cylindrical tube with a sensing element. The sensing element typically would be a solid state device, but other types of sensors could be used. Power and communication to the pressure sensor 170 are provided by means of pressure sensor communication cable 403.

One advantage of the system 100 is the ability to determine accurate measurements of the vapor pressure of multi-component liquids with the aid of the plunger 200, which can be positioned within the chamber 150 and then retracted at a uniform speed using the synchronized electric shaft drive motor 190.

The shaft drive motor 190 is typically equipped with a speed reducer or shaft reduction gear to bring the motor speed to a low rpm so that the plunger 200 retracts at a consistent, very low speed that is preferably in the order of about one inch per minute to about 0.1 inch per minute. The drive shaft motor 190, shaft reduction gear 190 and plunger 200 are meant by way of example and are not intended to limit the scope of the invention. Other apparatuses that provide the desired results (retraction of the plunger at a uniform, pre-selected speed) can be used. For example, the drive motor 190 could be a synchronous electric motor with an operator selectable drive frequency. In such a case, the plunger position could be determined directly as a function of motor operation time from a fixed starting point. Another means of plunger actuation could be an electrical linear motor.

One embodiment of the motor 190 and its mounting on the chamber 150 is shown in FIG. 3, where the motor mounting bracket 70 has a symmetric elongated U-shape with square corners and coplanar outwardly extending mounting ears at its open end. Each ear is centrally penetrated by a through hole for engagement by a motor bracket mounting screw, while a centrally positioned through clearance hole for permitting free passage of plunger 200 is located at the bottom of the U-shaped profile. Symmetrically positioned holes in the bottom of the U-shaped profile straddle the clearance hole and each can be engaged by the motor mounting screws 78 so that the hollow shaft drive motor 190 and the non-rotation key ring 76 can be mounted to the motor bracket 70. The motor mounting bracket 70 is attached to the side of chamber 150 symmetrically about the plunger port 18. The attachment of bracket 70 is by means of motor bracket mounting screws threadedly engaged with the tapped mounting holes in the chamber 150.

Figure 5:
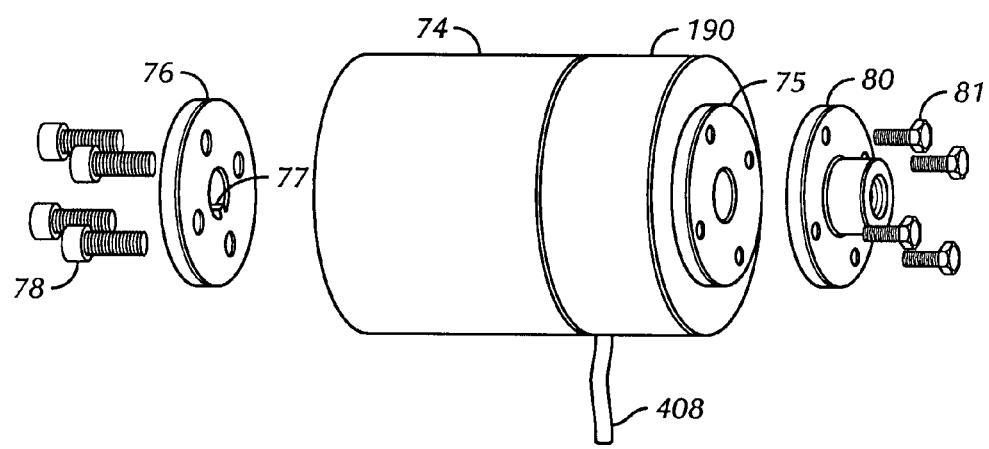
FIG. 5 is an oblique partially exploded view of one embodiment of the non-rotation key ring, the shaft reduction gear mounted on a face of the motor, and the drive nut.

Hollow shaft drive motor 190 is integrally mounted with hollow shaft reduction gear unit 74, seen in FIGS. 3 and 5. Hollow shaft motor/reduction gear sets are commercially available and are not specifically described herein. Motor 190 is provided with either a resolver or an encoder and is connected to a commercially available variable speed drive (not shown) by means of motor power and communication cord 408. The relative rotational position relative to an arbitrary reference position and the speed of the hollow shaft of motor 190 can be monitored and controlled by means of the variable speed drive. The reduction gear unit 74 is mounted by means of a regular pattern of drilled and tapped holes on a first transverse face to both the motor bracket 70 and the non-rotation key ring 76 by means of motor mounting screws 78.

The non-rotation key ring 76 is a short right circular annular cylindrical ring having a radially inwardly extending rectangular key 77 in its central hole. The inner diameter of the central hole of ring 76 is a clearance fit to the plunger 200, while the key 77 is a sliding fit to the plunger non-rotation keyway 87 of the plunger. The non-rotation key ring has mounting holes on the same pattern as those of the first transverse face of reduction gear unit 74 and the holes at the bottom of U-shaped motor bracket 70. The non-rotation key ring 76 is rigidly mounted between the motor bracket 70 and the first transverse face of the gear unit 74 by means of motor mount screws 78.

As shown in FIG. 5, the second traverse face of the integral hollow shaft reduction gear unit 74 is mounted to the first transverse face of motor 190. The output shaft of motor 190 and the input shaft of reduction gear unit 74 are coupled, while the hollow output shaft 75 has an outwardly extending flange on the exposed end of the motor 190. The flange of the output shaft 75 is provided with a regular array of drilled and tapped mounting screw holes.

Drive nut 80 is an internally threaded short right circular cylinder having an outwardly extending transverse flange at one end. The drive nut 80 is provided with mounting holes in a pattern corresponding to that on the output shaft 75 of reduction gear unit 74. Drive nut 80 is rigidly mounted to the drilled and tapped holes on the flange of the output shaft 75 by means of drive nut mounting screws 81.

A preferred embodiment of plunger 200, best seen in FIGS. 2 and 3, is an elongated cylindrical rod having a long polished cylindrical surface at a first end, a long plunger non-rotation keyway 87 in its central portion, and a helical drive thread 86 at a second end. The lengths of the keyway 87 and the drive thread 86 are generally comparable, while the polished cylindrical surface of plunger 200 is longer than the keyway or drive thread. The diameter of the plunger is such that it is a slip fit in both the smallest bore of the plunger port 18 of the chamber 150 and in the hollow shafts of the motor 190 and its integral reduction gear unit 74. The keyway 87 has a slip fit with the key 77 of the non-rotation key ring 76, while the drive thread 86 is threadedly engaged with the female threads of the drive nut 80. Because plunger 200 is constrained against rotation by the engagement of its keyway 87 with the key 77 of rigidly mounted non-rotation key ring 76, selective rotation of motor 190 and its driven output shaft 75 causes the plunger to be axially reciprocated relative to the motor.

Figure 8:
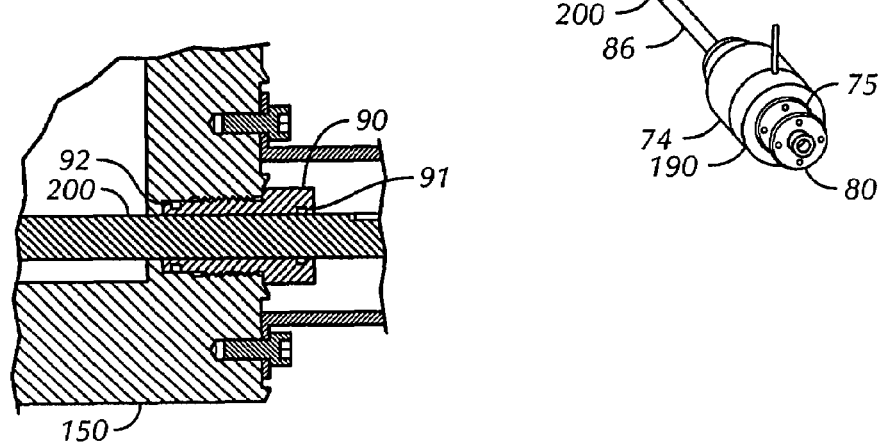
FIG. 8 is a side view of one embodiment of the plunger fitting.

The plunger fitting 90, illustrated in FIG. 8, contains an O-ring 92 used to seal between the plunger 200 and the plunger port 18 of the chamber 150 so that the plunger can be reciprocated in and out of the chamber internal volume without leakage. Plunger fitting 90 is a tubular sleeve having a through bore which is a close slip fit to the cylindrical polished portion of the plunger 200. An O-ring groove containing a plunger seal O-ring 91 is located near an external end of the through bore of the plunger fitting 90 and provides sealing between the reciprocable plunger 200 and the plunger fitting 90. The interior end of the plunger fitting 90 has an O-ring groove holding O-ring 92, a threaded segment with a larger diameter than the first section having O-ring 92, and a short regular hexagonal segment for wrenching purposes. The first segment of plunger fitting 90 is a close slip fit to the intermediate straight bore of the plunger port 18 of the chamber 150, so that the plunger fitting O-ring 92 can seal between the plunger fitting and the chamber 150. The threaded portion of the plunger fitting 90 is threadedly engaged with the threads in the plunger port 18 so that the plunger fitting is retained in the chamber 150.

Although not necessarily shown in the Figures, the entire system 100 is furnished with sealing devices such as seals, gaskets, and O-rings wherever necessary to prevent leaks within the system 100 and to minimize friction of the moving parts. In addition, the figures do not show a fluid source, or a sump for discarded fluid samples. These elements have not been shown, but the functions of these elements can be provided by a variety of standard commercially available hardware well known in the state of the art. The use of few moving parts in the system 100 is advantageous in that it minimizes costs and maintenance of the system 100.

Control of the system is provided by a control means 400 which may be a programmable linear controller (PLC), a computer, or a manual switching device. The control means 400, schematically shown in FIG. 1, provides a control and recording or data plotting system for operating the system and recording and/or plotting the generated data. The control means 400 communicates with the system components such as the temperature stabilizer 205 along a temperature communication cable 401 (for adjusting the temperature of the temperature stabilizer 205, such as the heating element 210), the purge valve 220 along a purge valve communication cable 402 (for opening and closing the purge valve 220), the intake valve 140 along an intake valve communication cable 404 (for opening and closing the intake valve), a bypass valve 113 along a bypass valve communication cable 407 (for opening and closing the bypass valve), and the drive motor 190 along a motor communication cable 408 (for controlling the position of the plunger 200).

Operation of the Vapor Pressure Determination System

The operation of the true vapor pressure determination system 100 of the present invention involves the isolation of a liquid sample in the closed chamber assembly 10, initial stabilization of the temperature and pressure of the sample at a predetermined value, and then a gradual reduction of the sample pressure by means of the synchronous withdrawal of the plunger 200 and communicated to the control means 400 via communication cable 403. The plunger position is also continuously monitored and communicated to the control means 400 via the communication cable 405. The sample pressure is measured continuously by pressure sensor 170 during the withdrawal of the plunger 200.

Figure 6:
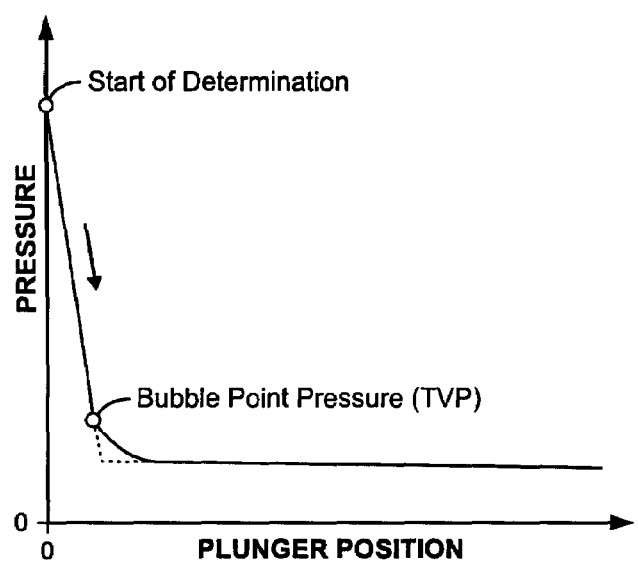
FIG. 6 shows a plot of pressure versus plunger displacement for a true vapor pressure determination using the vapor pressure determination system.

Initially the pressure will be reduced in a smooth, approximately linear relationship to plunger position, as seen in FIG. 6. However, when the pressure reaches the bubble point for the most volatile constituent of the fluid sample, that constituent begins to vaporize, thereby reducing the decrease in pressure with the plunger position. Accordingly, whenever an inflection point (i.e., a point of discontinuity in the rate of change in pressure with the retraction of the plunger) is found on the pressure versus plunger position curve, the pressure at that inflection point corresponds to the true vapor pressure for the liquid sample.

The control of the apparatus of the true vapor pressure determination system 100 is managed by a control device 400 which may be a computer or programmable linear controller (PLC) device, although manual control is also feasible for this relatively simple system. The control device 400 selectively applies power to the actuators connected with the liquid intake valve 140, the purge valve 220, and the bypass valve 113 to effect their switching on/off. Likewise, the control device controls the operation of the electrical drive motor 190 through an intermediate motor controller. Additionally, the control device energizes the temperature stabilizer 205, the temperature sensor 180, and the pressure sensor 170, as well as monitoring and recording their outputs. The operational parameters for the system 100 are generally operator determined through inputs to the control device.

Figure 7:
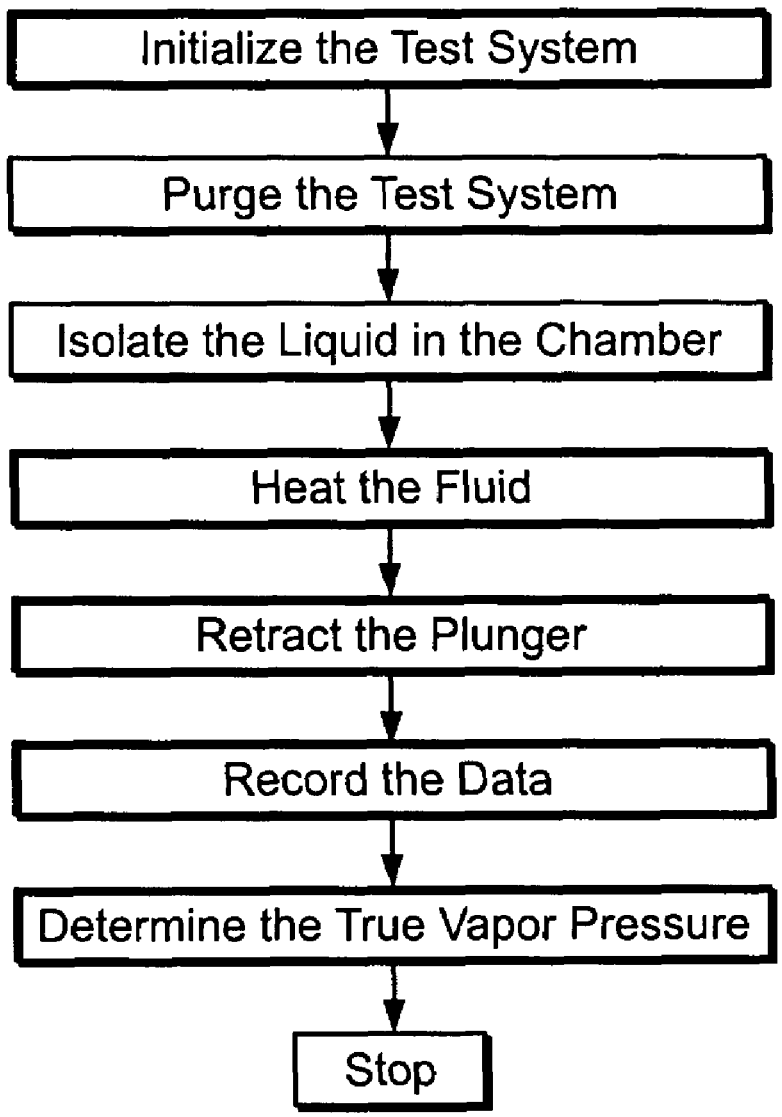
FIG. 7 is a flow chart of one embodiment of a method of determining the true vapor pressure using the vapor pressure determination system of the present invention.

The sequence of basic operational steps in the determination of true vapor pressure using the system 100 is shown in the flow chart of FIG. 7.

First, the operator initializes the test system 100 by initiating the flow of the test fluid through the chamber assembly 10. To initiate fluid flow through the chamber assembly 10 the operator opens the purge valve 220 and the intake valve 140. The liquid (not shown) to be tested for vapor pressure enters the chamber assembly 10 through the intake line 120 whenever the intake valve 140 is in the open position and leaves the chamber assembly 10 through the purge line 130 when the purge valve 220 is in the open position.

The chamber assembly is then purged by actuating the motor 190 to fully extending the plunger 200 into the chamber assembly 10. Once the plunger 200 is fully extended into the chamber assembly 10, the plunger position is set to zero and the bypass valve 113 is closed. The fluid is continually flushed through the chamber assembly 10 to purge the test system 100 of any residual fluid from the previous testing cycle, which typically takes from about 10 seconds to about 300 seconds.

Once the test system has been purged, the sample liquid for testing will be isolated in the chamber assembly 10 by closing the purge valve 220 and the intake valve 140. Once the purge valve 220 and the intake valve 140 are closed, the bypass valve 113 is opened to allow the fluid to continue to circulate by bypassing the test system.

Next the operator will select the desired temperature for the fluid in the chamber assembly 10 during the test cycle and activate the temperature stabilizer 205 to bring the fluid to the predetermined temperature. Normally, the sample fluid will be at a temperature below that at which it will be tested. To raise the sample temperature, power is applied to the temperature communication cable 401 of the heating element 210. The temperature of the liquid test sample isolated in the chamber assembly 10 is regulated by a controller (not shown) in the heating element 210 or, alternatively, a precision thermostat. The temperature is maintained and monitored throughout the test by the temperature sensor 180 which is in fluid communication with the liquid being tested. The pressure sensor 170 is used to measure the starting pressure, which must be above the bubble point for the sample liquid.

The data taken during the retraction of the plunger 200 is recorded on a recording device (schematically shown as part of the control device 400). The data recording device is started and the starting temperature, sample pressure, time, and plunger position (arbitrarily set at zero initially) are recorded. The drive motor 190 is then activated to rotate the drive nut 80, which is engaged with the helical drive threads 86 of the plunger 200. Because the plunger 200 is prevented from rotation by the engagement of its non-rotation keyway 87 by the non-rotation key 77 of the stationary non-rotation key ring 76, the plunger is caused to axially reciprocate by the motor rotation. The drive motor 190 is operated to withdraw the plunger 200 at a synchronized, pre-selected speed while the intake and purge valves 140 and 220, respectively, remain closed.

The drive motor 190 stops the outwardly movement of the plunger 200 when the plunger 200 is fully retracted and the test ends. This operation generally requires between 30 seconds to an hour, dependent upon the fluid parameters such as viscosity, composition, and the selected sample test temperature. This timing is meant by way of example and is not meant to limit the scope of the invention.

The withdrawal of the plunger 200 leads to an increase of volume of the liquid inside the chamber assembly 10, leading to an attendant pressure decrease for the liquid in the test sample. The withdrawal rate of plunger 200 is selected to be sufficiently slow to ensure the sample fluid constituents will be able to vaporize and will be near equilibrium when their true vapor pressure (i.e., the bubble point) is reached and that the fluid sample will remain at a constant temperature. The relatively small diameter of the plunger 200, along with its relatively long travel capability, allows the operator to maintain a slow, constant withdrawal rate for the plunger 200 with attendant minimal increments in pressure change.

The pressure in the chamber assembly 10 and the plunger position are recorded and plotted as shown in FIG. 6. The collected data is recorded concurrently with the retraction of the plunger 200. The system pressure and plunger position, measured by the pressure sensor 170 and the positional sensors for the drive motor 190, respectively, are continuously recorded. Backlash in the motor drive is not significant because the plunger 200 is outwardly biased against the threads of the drive nut 80 by the pressure internal to the chamber. This pressure bias on the plunger 200 permits an accurate measurement of the plunger position with use of the rotary position sensors of the motor 190.

Pressure, time and positions of the plunger 200 are recorded and/or plotted throughout the test cycle at operator-selected intervals on a control means 400 such as a mechanical chart and/or on a computer for use by the operator. The data collected is typically plotted electronically on the computer or on the mechanical chart of the programmable control means 400. The true vapor pressure (TVP) is determined from the graphical and/or numerical determination of the slope of the system pressure versus plunger position or time curve. When an inflection point in the pressure versus plunger position curve (i.e., a change in the slope of the curve) occurs, the bubble point pressure of the chamber assembly 10 is noted. This absolute pressure is the true vapor pressure of the fluid sample. At this point, the determination of the true vapor pressure for the fluid sample is complete.

The determination of the true vapor pressure in pure liquid or a multi-component liquid is very important for the processing of such liquid. One reason for measuring vapor pressure of liquid is to assure that the available net positive suction head of a pump is not less than the required suction head to prevent cavitations and pump damage. Another reason for measuring vapor pressure is to predict how much vapor would escape emission through the vents in storage tanks or during ship loading operations. Still another very important use of a vapor pressure analyzer is to determine the flash point of flammable liquids to determine how safely they can be handled.

Advantages of the Vapor Pressure Determination System

The primary advantage of the system 10 is its ability to rapidly determine accurate measurements of the true vapor pressure of multi-component liquids with the aid of the plunger 200, which can be positioned within the chamber assembly 10 and then retracted at a uniform speed using the drive motor 190 and drive nut 80 acting on the helical drive threads 86 of the non-rotating plunger. The motor 190 is equipped with the integral reduction gear unit 74 both to increase the motor torque and to lower the drive nut 80 rotational speed so that the plunger 200 retracts at a predetermined, consistent low speed on the order of about one inch per minute or less. Preferred embodiments of the system 10 retract the plunger 200 at a synchronous rate of from about one inch per minute to about 0.1 inch per minute. The use of few moving parts in the system 100 also is an advantage and minimizes maintenance of the system 100. Additionally, the seals of the system are easy to replace when necessary.

The system 100 is particularly suitable for sampling and testing crude oil and petroleum products because of its controllability over a wide range of test conditions and its sensitivity resulting from the use of the long, small diameter plunger 200.

The foregoing has outlined several embodiments of the vapor pressure determination system. However, it should be appreciated by those skilled in the art that the conception and the specific embodiment disclosed might be readily utilized as a basis for modifying or redesigning the system or method described for carrying out the same purposes as the invention. It should be realized by those skilled in the art that such equivalent constructions do not depart from the spirit and scope of the invention as set forth in the appended claims.

What is claimed is:

1. An apparatus for the determination of the vapor pressure of a liquid at a selected temperature comprising:
   a chamber having a fixed volume and designed to receive and isolate a sample of the liquid to be tested for a vapor pressure determination;
   a reciprocating plunger wherein the reciprocating movement of the plunger into and out of the chamber changes the volume of the liquid in the chamber;
   wherein the chamber is cylindrical with a vertical axis;

wherein the plunger reciprocates along an axis that is transverse to the vertical axis a motor for withdrawing the plunger from the chamber in a continuous movement and at a synchronous speed;

a pressure sensor sensing the vapor pressure in the chamber;

a temperature sensor for sensing the temperature of the liquid within the chamber; and a temperature stabilizer in communication with the temperature sensor.

2. The apparatus of claim 1, wherein the motor is equipped with a speed reducer allowing the plunger to be moved at about one inch per minute or less.

3. The apparatus of claim 1, wherein the motor is a shaft drive motor.

4. The apparatus of claim 1, wherein the motor withdraws the plunger from the chamber at a speed of about 1 inch per minute to about 0.1 inch per minute.

5. The apparatus of claim 1, wherein the motor has a reduction gear integrally mounted to the motor.

6. The apparatus of claim 1, wherein the chamber diameter is at least 3 times greater than a length of the vertical axis.

7. The apparatus of claim 1, further comprising a liquid intake line, a liquid purge line, and a bypass line connected to the chamber, wherein the intake line, purge line and bypass lines are selectably closed.

8. The apparatus of claim 1, further comprising a control device in communication with the motor, the temperature sensor, the pressure sensor and the temperature stabilizer.

9. A method of using the apparatus of claim 1 to determine the vapor pressure of a liquid at a pre-selected temperature within a range of temperatures comprising the steps of:

purging the apparatus of all liquids from previous tests;

extending the plunger into the chamber;

isolating a sample of the liquid for the vapor pressure determination within the chamber;

equilibrating the liquid in the chamber to a desired temperature using the temperature stabilizer;

activating the motor so that the plunger retracts from the chamber in a continuous movement at a synchronous speed;

taking measurements of the plunger position and the chamber pressure while the plunger is retracting;

recording the measurements in a curve plot of the chamber pressure versus the plunger position; and identifying the point of inflection in the curve plot as the true vapor pressure.

10. The method of claim 9, wherein the plunger is retracted at a rate ranging from about 1 inch per minute to about 0.1 inch per minute.

11. An apparatus for the determination of the vapor pressure of a liquid at a selected temperature comprising:

a chamber having a fixed volume capacity and a central vertical axis, wherein the chamber is designed to receive and isolate a sample of the liquid to be tested for a vapor pressure determination;

a reciprocating plunger positioned in the chamber such that the reciprocating movement of the plunger is transverse to the central axis of the chamber and changes the volume of the liquid in the chamber;

a withdrawing means for withdrawing the plunger from the chamber in a continuous movement and at a synchronous speed;

a temperature stabilizing means for maintaining the temperature of the liquid in the test chamber at a selected substantially constant temperature within a range of desired temperatures, wherein the means comprises a temperature sensor for sensing the temperature of the liquid within the test chamber and a heating element responsive to the temperature sensor;

a pressure sensor for reporting the vapor pressure in the chamber;

a liquid intake line connected to the chamber to receive the liquid for the vapor pressure test; and a liquid purge line connected to the chamber to purge the liquid after each test.

12. The apparatus of claim 11, wherein the motor is equipped with a speed reducer allowing the plunger to be moved at about one inch per minute or less.

13. The apparatus of claim 11, wherein the withdrawing means is a shaft drive motor with a reduction gear integrally mounted to the motor.

14. The apparatus of claim 11, wherein the withdrawing means withdraws the plunger from the chamber at a speed of about 1 inch per minute to about 0.1 inch per minute.

15. The apparatus of claim 11, wherein the chamber has a width to height ratio of 3.0 or more.

16. The apparatus of claim 11, wherein the chamber is cylindrical and wherein a chamber diameter is at least 3 times greater than a length of the vertical axis.

17. The apparatus of claim 16, further comprising a control device in communication with the withdrawing means, the temperature stabilizing means, the pressure sensor and a data recording means.

18. An apparatus for the determination of the vapor pressure of a liquid at a selected temperature comprising:

a cylindrical chamber having a fixed volume and designed to receive and isolate a sample of the liquid to be tested for a vapor pressure determination, wherein the chamber has a diameter that is three or more times a length of a central vertical axis of the chamber;

a reciprocating plunger wherein the reciprocating movement of the plunger into and out of the chamber is along an axis that is transverse to the central vertical axis which changes the volume of the liquid in the chamber;

a pressure sensor sensing the vapor pressure in the chamber;

a temperature sensor for sensing the temperature of the liquid within the chamber;

a heating element in communication with the temperature sensor;

a liquid intake line connected to the chamber, the intake line having a liquid intake valve for selectably controlling liquid flow into the chamber;

a liquid purge line connected to the chamber, the purge line having a liquid purge valve for selectably controlling liquid flow from the chamber; and a control device in communication with the motor, the temperature sensor, the pressure sensor, and the heating element.

19. The apparatus of claim 18, further comprising a data recording device for tracking changes in the chamber pressure versus changes in the plunger position or time.

20. A method of using the apparatus of claim 19 to determine the vapor pressure of a liquid at a pre-selected temperature within a range of temperatures comprising the steps of:

opening the liquid purge valve;

opening the liquid intake valve;

extending the plunger into the chamber;

close the bypass valve;

purge the chamber of prior liquid samples;

closing the liquid purge valve;

closing the intake valve when the chamber is full of the liquid for the vapor pressures determination and the pressure in the chamber is greater than the bubble-point pressure;

opening the bypass valve;

heating the liquid in the chamber to a desired temperature using the heating element;

maintaining the desired temperature in the chamber;

activating the motor so that the plunger retracts from the chamber in a continuous motion at a pre-selected synchronous speed until the pressure in the chamber is less than the bubble-point pressure at the desired temperature of the liquid;

taking measurements of the time, the plunger positions and the chamber pressure while the plunger is retracting;

recording the decrease in chamber pressure versus the retracting plunger position in a curve plot; and identifying the point of inflection in the curve plot as the true vapor pressure.

* * * * *